United States Patent [19]

Rusay

[11] Patent Number: 4,488,897
[45] Date of Patent: Dec. 18, 1984

[54] DICHLOROMETHYL OXADIAZOLE HERBICIDE ANTIDOTES

[75] Inventor: Ronald J. Rusay, Lafayette, Calif.

[73] Assignee: Stauffer Chemical Company, Westport, Conn.

[21] Appl. No.: 529,804

[22] Filed: Sep. 6, 1983

[51] Int. Cl.³ .................... A01N 43/82; C07D 87/38
[52] U.S. Cl. ......................................... 71/92; 548/143
[58] Field of Search ............................ 548/143; 71/92

[56] References Cited

U.S. PATENT DOCUMENTS 3,502,668  3/1970  Palazzo et al. .................. 548/143
4,243,409  1/1981  Schmidt et al. .................... 71/92

OTHER PUBLICATIONS

Lancelot et al., Chem. Abst. 94: 47221d.

*Primary Examiner*—Donald G. Daus
*Assistant Examiner*—Cecilia Shen
*Attorney, Agent, or Firm*—Leona L. Lauder

[57] ABSTRACT

A novel class of 2-dichloromethyl-5-phenyl or substituted phenyl 1,3,4-oxadiazole compounds having the formula

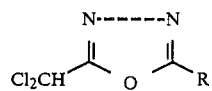

wherein R is unsubstituted phenyl or phenyl mono-, di-, or tri-substituted with halogen, hydroxy or nitro, which are useful as antidotes for thiocarbamate herbicidal crop injury.

8 Claims, No Drawings

DICHLOROMETHYL OXADIAZOLE HERBICIDE ANTIDOTES

FIELD OF INVENTION

This invention relates to a novel class of compounds, namely, 2-dichloromethyl-5-phenyl or substituted phenyl 1,3,4-oxadiazoles, useful as antidotes for thiocarbamate herbicidal crop injury when applied in a variety of methods.

BACKGROUND OF THE INVENTION

An herbicide is a compound which adversely controls or modifies plant growth, e.g., killing, retarding, defoliating, desiccating, regulating, stunting, tillering, stimulating, and dwarfing. The term "plant" refers to all physical parts of a plant, including seeds, seedlings, saplings, roots, tubers, stems, stalks, foliage, and fruits. "Plant growth" includes all phases of development from seed germination to natural or induced cessation of life.

Herbicides are generally used to control or eradicate weed pests. They have gained a high degree of commercial success because it has been shown that such control can increase crop yield and reduce harvesting costs.

Thiocarbamate herbicides are particularly effective in the control of grassy type weeds which interfere with the cultivation of a wide variety of crops, e.g. barley, corn, cotton, lentils, peanuts, peas, potatoes, soybeans, spinach, tobacco and tomatoes. Frequently the effective use of these herbicides requires the addition of an antidote compound.

The most popular methods of herbicide application include: preplant incorporation into the soil; in-furrow application to seeds and surrounding soil; pre-emergence surface treatment of seeded soil; and post-emergence treatment of the plant and soil.

A manufacturer of an herbicide generally recommends a range of application rates and concentrations calculated to maximize weed control. The range of rates varies from approximately 0.01 to 50 pounds per acre (0.0112 to 56 kilograms per hectare (k/ha)), and is usually in the range of from 0.1 to 25 pounds per acre (0.112 to 28 k/ha). The term "herbicidally effective amount" describes the amount of an herbicide compound which controls or modifies plant growth. The actual amount used depends upon several considerations, including particular weed susceptibility and overall cost limitations.

While many herbicides are immediately toxic to a large number of weed pests, it is known that the effect of many herbicides upon important plant cultivations is either non-selective or not adequately selective. Thus, many herbicides damage not only the weeds to be controlled, but to a greater or lesser extent, the desirable cultivated plants as well. This holds true for many herbicidal compounds which have been commercially successful and are commercially available. These herbicides include types such as triazines, urea derivatives, halogenated acetanilides; carbamates, thiocarbamates, thiocarbamate sulfoxides, pyrrolidinones, p-toluidines, and the like. Some examples of these compounds are described in U.S. Pat. Nos. 2,891,855, 2,913,237, 3,037,853, 3,175,897, 3,185,720, 3,198,786, 3,442,945, 3,582,314, 3,780,090, 3,952,056 4,110,105, and 3,257,190.

The side effect of injury to a cultivated crop by various herbicides is particularly inconvenient and unfortunate. Thiocarbamate herbicides can sometimes cause serious malformation and stunting of crop plants. This abnormal growth in the crop plants results in loss of crop yield.

To preserve the beneficial aspects of herbicide use, i.e., to maximize weed control, and to minimize crop damage, many herbicide antidotes have been prepared. These antidotes reduce or eliminate damage to the crop while maintaining or increasing the damaging effect of the herbicide on weed species. (See, for example, U.S. Pat. Nos. 3,959,304; 4,021,224 and 4,021,229 and Belgian Pat. No. 846,894.)

The precise mechanism by which an antidote reduces herbicidal crop injury has not been established. An antidote compound may be a remedy, interferent, protectant, or antagonist. As used herein, "antidote" describes a compound which has the effect of establishing herbicide selectivity, i.e., continued herbicidal phytotoxicity to weed species and reduced or non-phytotoxicity to cultivated crop species. The term "antidotally effective amount" describes the amount of an antidote compound which counteracts a phytotoxic response of a beneficial crop to an herbicide.

DESCRIPTION OF THE INVENTION

It has now been discovered that a novel class of compounds, 2-dichloromethyl-5-phenyl or substituted phenyl 1,3,4-oxadiazoles, are effective as antidotes for the protection of a variety of crops from thiocarbamate herbicide injuries. Such antidotal effects as decreasing crop injury and increasing crop tolerance to such herbicides occur when the herbicides and oxadiazole antidotes are applied in a variety of ways, together in a tank-mix, sequentially or in combination with other compounds.

The 2-dichloromethyl-5-phenyl or substituted phenyl 1,3,4-oxadiazoles of the instant invention are considered novel and correspond to the following formula:

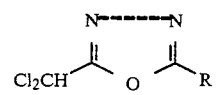

wherein R is unsubstituted phenyl or phenyl mono-, di-, or tri-substituted with halogen, hydroxy or nitro.

Preferred of the oxadiazole compounds disclosed herein are those in which R is unsubstituted phenyl, and phenyl mono- or disubstituted with halogen or hydroxy.

Further preferred of such oxadiazoles are those in which R is unsubstituted phenyl and phenyl di-substituted with halogen and mono-substituted with hydroxy.

This invention also embodies a two-part herbicidal system comprised of (a) an herbicidally effective amount of a thiocarbamate compound of the formula

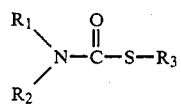

in which $R_1$ is alkyl having 1–6 carbon atoms, inclusive;
$R_2$ is selected from the group consisting of alkyl having 1–6 carbon atoms, inclusive; and cyclohexyl; or R₁ and R₂ form indistinguishable parts of a single alkylene ring having 4–10 carbon atoms, inclusive; and R₃ is selected from the group consisting of alkyl having 1–6 carbon atoms, inclusive; haloalkyl wherein halo is selected from the group consisting of chlorine, bromine and iodine and alkyl has 1–6 carbon atoms, inclusive; alkenyl having 2–6 carbon atoms, inclusive; haloalkenyl wherein halo is selected from the group consisting of chlorine, bromine and iodine and alkenyl has 2–6 carbon atoms, inclusive; benzyl; and halo-substituted benzyl, wherein halo is selected from the group consisting of chlorine, bromine and iodine; and (b) a non-phytotoxic antidotally effective amount of a compound of the formula

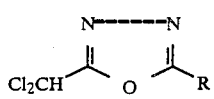

wherein R is unsubstituted phenyl or phenyl mono-, di-, or tri-substituted with halogen, hydroxy or nitro.

The preferred oxadiazole compounds of such two-part herbicidal systems are those discussed above.

The preferred thiocarbamate herbicides of such two-part herbicidal systems are those in which R₁, R₂ and R₃ are each independently C₁–C₆ alkyl.

By way of exemplification, the active thiocarbamate herbicides employed in the invention may include the following: S-ethyl N,N-dipropyl thiocarbamate, S-ethyl N,N-diisobutyl thiocarbamate, S-propyl N,N-dipropyl thiocarbamate, S-propyl N,N-butylethyl thiocarbamate.

This invention also relates to a method of controlling undesirable vegetation and at the same time reducing thiocarbamate herbicidal crop injury which comprises applying to the locus where control is desired a composition comprising:

(a) an herbicidally effective amount of a thiocarbamate compound of the formula

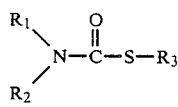

in which

R₁ is alkyl having 1–6 carbon atoms, inclusive;

R₂ is selected from the group consisting of alkyl having 1–6 carbon atoms, inclusive; and cyclohexyl; or R₁ and R₂ form indistinguishable parts of a single alkylene ring having 4–10 carbon atoms, inclusive; and R₃ is selected from the group consisting of alkyl having 1–6 carbon atoms, inclusive; haloalkyl wherein halo is selected from the group consisting of chlorine, bromine and iodine and alkyl has 1–6 carbon atoms, inclusive; alkenyl having 2–6 carbon atoms, inclusive; haloalkenyl wherein halo is selected from the group consisting of chlorine, bromine and iodine and alkenyl has 2–6 carbon atoms, inclusive; benzyl; and halo-substituted benzyl, wherein halo is selected from the group consisting of chlorine, bromine and iodine; and (b) a non-phytotoxic antidotally effective amount of a compound of the formula

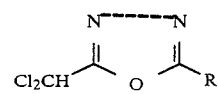

wherein R is unsubstituted phenyl or phenyl mono-, di-, or tri-substituted with halogen, hydroxy or nitro.

The locus where control and herbicidal crop injury reduction is desired may include soil, seeds, seedlings and vegetation.

PREPARATION

In general, the active antidote compounds of the present invention can be prepared by the following method.

N-isopropyl dichloroacetimidoyl chloride is reacted with the appropriately substituted aryl hydrazide in toluene and refluxed. The toluene is then evaporated leaving the product, which is recrystallized.

The compounds of the present invention and their preparation are more particularly illustrated by the following examples. Following the examples of preparation is a table of compounds which can be prepared according to the procedures described herein. Compound numbers have been assigned to them and are used for identification throughout the balance of the specification.

EXAMPLE I

Preparation of 2-Dichloromethyl-5-phenyl-1,3,4-oxadiazole

Three and seventy-four hundredths grams (3.74 g) (20 millimoles) (mM) of N-isopropyl dichloroacetimidoyl chloride was dissolved in 100 milliliters (ml) of toluene and then 2.72 g (20 mM) of benzoyl hydrazide was added. The reaction mixture was refluxed with azeotropic removal of water for three hours. The mixture was cooled and filtered.

The toluene was evaporated off, yielding crystal plates which were recrystallized from hexane and washed with ethanol. The yield was 3.5 g (65%). The melting point is 76°–78° C. The structure was confirmed by mass spectrometry (MS), nuclear magnetic resonance (NMR) and infrared analysis (IR).

EXAMPLE II

Preparation of 2-Dichloromethyl-5-(2'-hydroxyphenyl)-1,3,4-oxadiazole

Three and seventy-four hundredths g (20 mM) of N-isopropyl dichloroacetimidoyl chloride and 3.04 g (20 mM) of salicyl hydrazide in 100 ml toluene was refluxed for three hours. The work-up followed the procedures of Example I.

The product yield was 2.2 g (46%). Its melting point was 99°–100° C. The structure was confirmed by NMR, IR and MS.

EXAMPLE III

Preparation of 2-Dichloromethyl-5-(2',4'-dichlorophenyl)-1,3,4-oxadiazole

Two and thirty-four hundredths g (12.4 mM) of N-isopropyl dichloroacetimidoyl chloride and 2.55 g (12.5 mM) of 2,4-dichlorobenzoyl hydrazide in 100 ml toluene was refluxed for three hours. The work-up followed the procedure of Example I.

The product yield was 1.62 g (43%). Its melting point was 68°-70°. The structure was confirmed by MS, NMR and IR.

TABLE I $$\text{Cl}_2\text{CH} \overset{\text{N}=\text{N}}{\underset{\text{O}}{\diagdown \diagup}} \text{R}$$

| Compound Number | R | Physical Constant m.p. (°C.) or $n_D^{30}$ |
|---|---|---|
| 1 | phenyl | 76-78 |
| 2 | 2-hydroxyphenyl (HO-) | 99-100 |
| 3 | 2,4-dichlorophenyl (Cl, Cl) | 68-70 |
| 4 | 4-nitrophenyl (NO₂) | 194-196 |
| 5 | 3-nitrophenyl (NO₂) | 75-76 |
| 6 | 2,3-dichlorophenyl (Cl, Cl) | 98-100 |

Representative Compounds 1-3 were tested according to the following procedures. The results are recorded in Tables II and III.

Testing

Stock solutions of the herbicides were prepared by diluting the requisite amount of each herbicide in water or in a 1:1 mixture of water and acetone. Stock solutions of each antidote were prepared at the desired concentrations by diluting the requisite amounts of each antidote in acetone.

The herbicide was incorporated into the soil prior to planting, that is, it was applied by pre-plant incorporation (PPI). The herbicide was either incorporated into the soil alone in preparation for in-furrow application (IF) of the antidote, or tank-mixed with the antidote solution prior to incorporation (PPI-TM).

The antidote solutions were applied to the soil either by in-furrow surface application or by pre-plant incorporation. In all cases of pre-plant incorporation, the antidote was tank-mixed with the herbicide prior to incorporation into the soil.

These methods of application are abbreviated in the Tables as follows:

IF=In-furrow surface application of antidote;
PPI-TM=Pre-plant incorporation of antidote, in tank-mix with herbicide; and
PPI=Pre-plant incorporation of the herbicide alone.

For in-furrow application, a one pint (473 cubic centimeter (cc)) sample of soil containing the previously incorporated herbicide was removed and retained from each planting flat. After leveling and furrowing the soil, seeds of the crop or weed species were planted ½ inch deep (1.27 centimeter). Each flat was divided in half by a wooden barrier. A stock solution of the antidote was atomized directly onto the exposed seeds and soil in the open furrow on one side of the barrier. The seeds in the entire flat were then covered with the previously removed soil. The antidotally untreated sections of flats were compared for observed differences which would indicate lateral movement of the antidote through the soil.

Control flats contained crops treated with herbicide only.

All flats were placed on greenhouse benches where temperature was maintained between 70° and 90° F. (21.1° to 32.2° C.). The flats were watered by sprinkling as needed to assure good plant growth.

All of the soil used in the tests described herein was loamy sand soil treated with 50 parts per million (ppm) each of a commercially available fungicide, N-[(trichloromethyl)-thio]-4-cyclohexene-1,2-dicarboximide, and 17-17-17 fertilizer, which contains 17% by weight equivalent each of nitrogen, phosphorus pentoxide, and potassium oxide.

Injury ratings were taken four weeks after application of the antidote. The effectiveness of the antidote was determined by visual comparison of crop injury which occurred in the test flats to that which occurred in the check flats which were not treated with herbicide or antidote.

The treated crops initially screened for diminution of herbicidal injury were milo, wheat (WHT), cotton (COT), rice, barley (BAR), corn and soybeans (SOY). The compound was also treated on the following weeds: watergrass (WG) (*Echinochloa crusgalli*) and foxtail (FT) (*Setaria viridis*).

The following are the herbicides with which the antidotes were tested:

VERNAM®—S-propyl N,N-dipropyl thiocarbamate, and
EPTAM®—S-ethyl-N,N-dipropyl thiocarbamate.

The results are indicated in Tables II and III by numbers separated by slashes, for e.g., *10/85. The first number is the percentage of injuries sustained by the indicated crop or weed species when treated by both the antidote and herbicide at the rates specified. The second number is the percentage of injuries sustained by the crop or weed species when treated by the herbicide alone at the rate specified. Thus, the number represents: Antidote treated/antidote untreated.

An asterisk (*) in Table II indicates that the antidote compound is active in reducing herbicidal injury to the crops.

All rates shown, for both herbicide and antidote, are in pounds per acre.

Injury Ratings

The injury to the crop (Table II) or weeds (Table III) is shown as a percentage of damage done to the plants as compared to an evaluation of the overall undamaged state of the plants untreated with either herbicide or antidote. The damage done to the plants is a function of the number of plants injured and the extent of injury to each plant. This rating is made four (4) weeks after application of the herbicide alone or of the herbicide in combination with the antidote.

chain fatty alcohols and alkali metal salts of the sulfated fatty alcohols; salts of sulfonic acid; esters of long chain fatty acids; and polyhydric alcohols, in which the alcohol groups are free, omegasubstituted polyethylene glycols of relatively long chain length. A list of surface active agents suitable for use in agriculture formulations can be found in Wade Van Valkenburg, *Pesticide Formulations* (Marcel Dekker, Inc., N.Y. 1973) at pages 79–84.

TABLE II

Antidotal Effectiveness

| Herbicide | | | Antidote | | | % Injury | | | | | | |
|---|---|---|---|---|---|---|---|---|---|---|---|---|
| Name | Rate lb/A | Method | Cmpd. No. | Rate lb/A | Method | Milo | Wheat | Cotton | Rice | Barley | Corn | Soybean |
| VERNAM | 1.25 | PPI | 1 | 5.00 | IF | 97/97 | 95/95 | 60/60 | 100/100 | 70/70 | | |
| VERNAM | 6.00 | PPI | 1 | 5.00 | IF | | | | | | 10*/85 | 40/40 |
| EPTC | 6.00 | PPI/TM | 1 | 5.00 | PPI/TM | | | | | | 0*/90 | |
| EPTC | 6.00 | PPI/TM | 1 | 0.50 | PPI/TM | | | | | | 30*/90 | |
| EPTC | 6.00 | PPI/TM | 1 | 0.05 | PPI/TM | | | | | | 90/90 | |
| VERNAM | 1.25 | PPI | 2 | 5.00 | IF | 90/90 | 80/80 | 55/55 | 65*/100 | 90/90 | | |
| VERNAM | 6.00 | PPI | 2 | 5.00 | IF | | | | | | 20*/90 | 55/40 |
| VERNAM | 1.25 | PPI | 3 | 5.00 | IF | 90/90 | 65*/80 | 60/55 | 50*/100 | 100/90 | | |
| VERNAM | 6.00 | PPI | 3 | 5.00 | IF | | | | | | 70*/90 | 40/40 |

TABLE III

Herbicidal Effectiveness

| Herbicide | | | Antidote | | | % Injury | | |
|---|---|---|---|---|---|---|---|---|
| Name | Rate lb/A | Method | Cmpd. No. | Rate lb/A | Method | Watergrass | Foxtail | Wild Oat | Shattercane |
| EPTC | 6.00 | PPI/TM | 1 | 5.00 | PPI/TM | 100/100 | 100/100 | | |
| EPTC | 6.00 | PPI/TM | 1 | 0.50 | PPI/TM | 100/100 | 100/100 | | |
| EPTC | 6.00 | PPI/TM | 1 | 0.05 | PPI/TM | 100/100 | 100/100 | | |

Test Results

Table II indicates that the representative compounds of this invention show good antidotal activity with a variety of crops, most notably corn. Table III indicates that the use of antidote compounds of this type did not result in a reduction of herbicidal injury to weeds.

Formulations

A formulation is the incorporation of a formulant in a form which is directly usable on crops and weeds. As defined herein, a "formulant" is the material which is to be formulated. The formulant may be either an antidote compound alone or an herbicide and antidote composition. The purpose of the formulation is to apply the formulant to the locus where it is desired to establish herbicidal selectivity by a convenient method. The "locus" may include soil, seeds, seedlings and vegetation.

The formulations are commonly dusts, wettable powders, granules, solutions or emulsifiable concentrates.

Dusts are free-flowing powder compositions containing the formulant impregnated on a particulate carrier. The particle size of the carriers is usually in the approximate range of 30 to 50 microns. Examples of suitable carriers are talc, bentonite, diatomaceous earth, and pyrophyllite. The composition generally contains up to 50% of formulant. Anti-caking and anti-static agents may also be added. Dusts may be applied by spraying from boom and hand sprayers on airplanes.

Wettable powders are finely divided compositions comprising a particulate carrier impregnated with the formulant and additionally containing one or more surface active agents. The surface active agent promotes rapid dispersion of the powder in an aqueous medium to form stable, sprayable suspensions. A wide variety of surface active agents can be used, for example, long Granules comprise the formulant impregnated on a particulate inert carrier having a particle size of about 1 to 2 millimeters (mm) in diameter. The granules can be made by spraying a solution of the formulant in a volatile solvent onto the granular carrier. Examples of suitable carriers for the preparation of granules include clay, vermiculite, sawdust, and granular carbon.

Emulsifiable concentrates consist of an oil solution of the formulant plus an emulsifying agent. Prior to use the concentrate is diluted with water to form a suspended emulsion of oil droplets. The emulsifiers used are usually a mixture of anionic and nonionic surfactants. Other additives, such as suspending agents and thickeners, may be included in the emulsifiable concentrate.

When the formulant is an antidote and herbicide composition, the proportion of antidote compound to herbicide compound generally ranges from approximately 0.001 to 30 parts by weight of the antidote compound per weight of the herbicide compound.

Formulations generally contain several additives in addition to the formulant and carrier or agent. Among these are inert ingredients, diluent carriers, organic solvents, water, oil and water, water in oil emulsions, carriers of dusts and granules, and surface active wetting, dispersing and emulsifying agents. Fertilizers, e.g., ammonium nitrate, urea and superphosphate, may be included. Aids to rooting and growth, e.g., compost, manure, humus and sand, may also be included.

Alternatively, the antidote compounds and herbicide and antidote compositions of this invention can be applied to a crop by addition of the formulant to irrigation water supplied to the field to be treated. This method of application permits the penetration of the compositions into the soil as the water is absorbed.

As another alternative, the formulant can be applied to the soil in the form of a solution in a suitable solvent. Solvents frequently used in these formulations include kerosene, fuel oil, xylene, petroleum fractions with boiling ranges above xylene and aromatic petroleum fractions rich in methylated naphthalenes. Liquid solutions, like dusts, may be applied by spraying from boom and hand sprayers on airplanes.

What is claimed is:

1. An herbicidal composition comprising:
(a) an herbicidally effective amount of a thiocarbamate compound of the formula

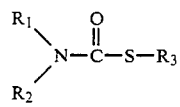

in which
$R_1$, $R_2$ and $R_3$ are each independently alkyl having 1–6 carbon atoms, inclusive; and
(b) a non-phytotoxic antidotally effective amount of a compound of the formula

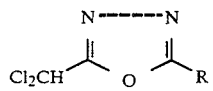

wherein R is unsubstituted phenyl or phenyl mono- or di-substituted with hydroxy or nitro.

2. An herbicidal composition according to claim 1 wherein R is unsubstituted phenyl or phenyl mono-substituted with hydroxy.

3. An herbicidal composition according to claim 1 wherein the thiocarbamate herbicide is S-ethyl-N,N-dipropyl thiocarbamate, and the antidote is 3-dichloromethyl-5-phenyl-1,3,4-oxadiazole.

4. A method of controlling undesirable vegetation and reducing thiocarbamate herbicidal crop injury comprising applying to the locus where control is desired a non-phytotoxic antidotally effective amount of a compound of the formula

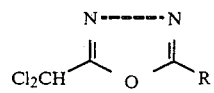

where R is unsubstituted phenyl or phenyl mono- or di-substituted with hydroxy or nitro.

5. A method according to claim 4 wherein R is unsubstituted phenyl or phenyl mono-substituted with hydroxy.

6. A metod of controlling undesirable vegetation and reducing herbicidal crop injury due to a thiocarbamate herbicide which comprises applying to the locus where control is desired an herbicidal composition comprising
(a) an herbicidally effective amount of a thiocarbamate compound of the formula

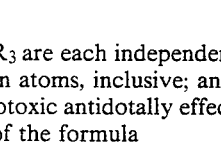

in which
$R_1$, $R_2$ and $R_3$ are each independently alkyl having 1–6 carbon atoms, inclusive; and
(b) a non-phytotoxic antidotally effective amount of a compound of the formula

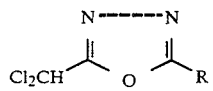

wherein R is unsubstituted phenyl or phenyl mono- or di-substituted with hydroxy or nitro.

7. A method according to claim 6 wherein $R_1$, $R_2$ and $R_3$ are each independently $C_1$–$C_6$ alkyl; and R is unsubstituted phenyl or 2'-hydroxy phenyl.

8. A method according to claim 7 wherein the thiocarbamate herbicide is S-ethyl N,N-dipropyl thiocarbamate and the antidote is 3-dichloromethyl-5-phenyl-1,3,4-oxadiazole.

* * * * *